United States Patent [19]

Symon et al.

[11] 4,433,194

[45] Feb. 21, 1984

[54] PURIFICATION OF CYCLOHEXANE

[75] Inventors: Ted Symon, Lombard; Dusan J. Engel, Des Plaines, both of Ill.

[73] Assignee: UOP Inc., Des Plaines, Ill.

[21] Appl. No.: 492,306

[22] Filed: May 6, 1983

[51] Int. Cl.$^3$ .................. B01D 3/34; C10G 29/12; C07C 17/38; C07C 21/00

[52] U.S. Cl. ..................... 585/803; 585/807; 585/827; 585/836; 585/853; 203/29; 203/32; 203/33; 208/249

[58] Field of Search ............... 585/803, 807, 827, 836, 585/853; 203/29, 32, 33, 45; 208/249

[56] References Cited

U.S. PATENT DOCUMENTS

| | | | |
|---|---|---|---|
| 2,846,485 | 8/1958 | Meason et al. | 203/29 |
| 2,891,100 | 6/1959 | Kron | 585/803 |
| 2,896,002 | 7/1959 | Souillard | 585/803 |
| 2,970,105 | 1/1961 | Condo et al. | 208/249 |
| 4,367,364 | 1/1983 | Kulprathipanza et al. | 585/826 |

*Primary Examiner*—Delbert E. Gantz
*Assistant Examiner*—Chung K. Pak
*Attorney, Agent, or Firm*—James R. Hoatson, Jr.; Raymond H. Nelson; William H. Page, II

[57] ABSTRACT

Solvents which may be used as mediums for the polymerization of olefinic hydrocarbons to form polymers useful as membranes in a gas separation process require purification to remove any impurities which will effect the aforesaid polymerization. Purification of these solvents such as cyclohexane may be effected by treating the solvent with titanium tetrachloride, contacting the solution with an adsorbent such as silica gel and thereafter distilling the solvent in the presence of a purification agent such as an alkaline metal aluminum hydride or borohydride.

8 Claims, No Drawings

PURIFICATION OF CYCLOHEXANE

BACKGROUND OF THE INVENTION

The use of semipermeable membranes for reverse osmosis or ultrafiltration processes is well known. For example, in a reverse osmosis process saline water may be passed through a semipermeable membrane which is permeable to water but relatively impermeable to salt, thereby separating the brine in the water from the water to afford relatively pure water which may be utilized for personal use such as drinking, cooking, etc.

In addition to the separation of liquids, certain membranes may also be utilized for the separation of various gases. The separation of a gas mixture utilizing a membrane is effected by passing a feed stream of the gas across the surface of the membrane. Inasmuch as the feed stream is at an elevated pressure relative to the effluent stream, a more permeable component of the mixture will pass through the membrane at a more rapid rate than will a less permeable component. Therefore, the permeate stream which passes through the membrane is enriched in the more permeable component while, conversely, the residue stream is enriched in the less permeable component of the feed.

This ability to separate gases from a mixture stream will find many applications in commercial uses. For example, gas separation systems may be used for oxygen enrichment of air, for improved combustion efficiencies and conservation of energy resources. Likewise, nitrogen enrichment of air may be applicable where inert atmospheres are required. Other applications for oxygen enriched gases may be improving selectivity and efficiency of chemical and metallurgical processes. Similarly, inert atmospheres such as may be provided for by this invention may also be utilized in chemical and metallurgical processes. Some other applications of gas separation would include helium recovery from natural gas, hydrogen enrichment in industrial process applications, and scrubbing of acid gases. Specific uses for oxygen enrichment of air would be breathing systems for submarines and other underwater stations, improved heart-lung machines, and other lung assist devices. Another specific application of a gas separation system would be in aircraft to provide oxygen enrichment for life-support systems and nitrogen enrichment for providing an inert atmosphere for fuel systems. In addition, gas separation systems may be used for environmental benefits, e.g. methane can be separated from carbon dioxide in waste gases from sewage treatment processes and oxygen enriched air can be produced to enhance sewage digestion.

Among the thin film polymers which may be used for gas separation membranes are the poly(methylpentenes). However, the methylpentene and particularly 4-methyl-1-pentene which is used to prepare the desired membrane must possess certain characteristics which will enable it to be utilized in the desired manner. Some prior methods to obtain a poly(methylpentene) utilized various catalysts to effect the polymerization. One prior method employs a Ziegler-Natta type catalyst. When utilizing a compound such as aluminum chloride in the polymerization reaction, the poly(methylpentene) is in the form of a sticky solid which is unsuitable for use in the preparation of membranes. Likewise, a catalyst comprising aluminum triisobutyl-titanium tetrachloride produces a low molecular weight solid but brittle polymer which is also unsuitable in the preparation of membranes. In a similar manner, commercial poly(methylpentene) when polymerized from 4-methyl-1-pentene uses a titanium chloride catalyst which has been activated with aluminum trialkyls, producing a polymer which is largely an isotactic material which possesses a poor solubility in solvents as well as being brittle and relatively opaque in nature.

In view of the disadvantages of the prior methods, it is necessary to effect the polymerization of 4-methyl-1-pentene under certain conditions whereby a polymer is obtained which may be utilized to prepare a membrane which will effectively act to separate various gases. In this respect, it has been discovered that undesirable characteristics present in the polymer which is obtained by the polymerization reaction may be traced to impurities which are present in the solvent which is employed as a medium in which the polymerization is effected. In order to overcome these disadvantages, it is necessary to utilize a solvent which is free from impurities which led to the preparation of unusable polymers.

As will hereinafter be shown in greater detail, it is now possible to purify a solvent such as cyclohexane whereby it may be effectively used in polymerization reactions involving olefins such as 4-methyl-1-pentene.

BRIEF SUMMARY OF THE INVENTION

This invention relates to a method for the purification of solvents. More specifically, the invention is concerned with a process or method for the purification of cyclohexane whereby undesirable impurities which cause a deleterious effect in the polymerization of olefins are effectively removed.

As was hereinbefore set forth, the separation of various gases from mixtures thereof may constitute an important advance in commercial applications, this advance becoming increasingly important in view of the necessity to conserve energy. One particular application which would apply relates to increasing the thermal efficiency of combustion processes when utilizing fossil fuels in commercial combustion applications. By utilizing a gas separation membrane in processes such as coal gasification, it may be possible to provide an oxygen-enrichment of air for the production of low and medium British Thermal Unit (BTU) reduction gases as well as an oxygen enrichment of air for the combustion of these gases. For example, by placing a gas membrane separation system in close proximity to both gas production and gas combustion facilities, it would allow a site-located oxygen enrichment plant to supply both processes without the additional expense of transporting the gas or duplicating any enrichment facilities. In view of this, it is necessary to provide a gas separation membrane which possesses excellent oxygen-nitrogen selectivities. One particular type of gas separation membrane which possesses this characteristic comprises poly(methylpentene). This membrane is prepared by polymerizing 4-methyl-1-pentene in the presence of a solvent medium, a particularly effective solvent comprising cyclohexane. However, the solvent must be free of any impurities which will effect the polymerization to form the desired product.

It is therefore an object of this invention to provide a method for the purification of solvents which are utilized in polymerization reactions.

A further object of this invention is to set forth a method for the purification of cyclohexane whereby undesirable impurities are removed therefrom.

In one aspect, an embodiment of this invention resides in a method for the purification of cyclohexane which comprises treating said cyclohexane with titanium tetrachloride, contacting said treated cyclohexane with an adsorbent, subjecting said cyclohexane to fractional distillation in the presence of a purification agent comprising an alkali metal borohydride or aluminum hydride to remove contaminants therefrom, and recovering the purified cyclohexane.

A specific embodiment of this invention is found in the method for the purification of cyclohexane which comprises treating said cyclohexane with titanium tetrachloride, contacting said treated cyclohexane with silica gel, subjecting said cyclohexane to fractional distillation at pressures in the range of from about subatmospheric to about atmospheric pressure in the presence of a purification agent comprising sodium borohydride to remove contaminants therefrom, and recovering the purified cyclohexane.

Other objects and embodiments will be found in the following further detailed description of the invention.

DETAILED DESCRIPTION OF THE INVENTION

As hereinbefore set forth, the present invention is concerned with a process for purifying solvents which are utilized in a polymerization process involving 4-methyl-1-pentene to obtain a poly(methylpentene) polymer which possesses the necessary characteristics which will enable it to be utilized in the preparation of a membrane, said membrane consisting of a finely permeable barrier composited on a finely porous support membrane which, if so desired, may be backed by a fabric. By utilizing an imperfection-free semipermeable membrane which has been prepared from the poly(methylpentene) prepared by a polymerization process involving a solvent medium which is free from impurities, it is possible to effect a gas separation process in which a selected gas or gases will pass through the barrier with little hindrance while other gases will be less able to penetrate the barrier. The polymerized poly(methylpentene) which is obtained from the polymerization reaction may be utilized as a homopolymer or, if so desired, copolymerized with a branched chain diolefinic hydrocarbon such as isoprene (2-methyl-1,3-butadiene), 2-methyl-1,3-pentadiene, 2-methyl-1,3-hexadiene, 2-methyl-1,3-heptadiene, 2-methyl-2,4-pentadiene, 2-methyl-2,4-hexadiene, etc. Both the homopolymerization and copolymerization of the reactants is effected in an organic solvent medium, the preferred solvent for the reaction of this invention comprising cyclohexane, although it is also contemplated that other organic solvents such as cycloheptane, cyclooctane, methylcyclopentane, methylcyclohexane, tetralin, hexane, heptane, octane, etc. may be employed, although not necessarily with equivalent results.

It is well known that polymerization reactions of olefinic hydrocarbons, such as the Ziegler-Natta type, are sensitive to various types of impurities. Inasmuch as the solvents which are utilized in these reactions are generally present in large quantities, it is imperative that the solvent be free of impurities inasmuch as the presence of the impurities will have a significant and deleterious effect regarding the degree of polymerization of the olefinic hydrocarbon as well as the structure of the polymer which is prepared, thus effecting its performance, in this case, as a membrane for the separation of gases. For example, in the polymerization process before synthesizing or polymerizing a solvent-soluble poly(4-methyl-1-pentene), to obtain an oxygen-enrichment membrane, any impurities which are present in the saturated linear aliphatic hydrocarbons or alicyclic hydrocarbons which are used as solvents can, to a great extent, influence the reaction rate of the polymerization and therefore the solubility of the solvent-soluble poly(methylpentene).

Impurities which may be present in the solvent may comprise isoparaffins, olefins, both internal and external in nature, aromatics, oxygen-and sulfur-containing compounds, as well as water. Each impurity will act in a different fashion to influence the polymerization of the desired olefin. For example, isoparaffins in general will act to slow down the reaction, while conversely, alpha-olefins will polymerize at a much faster rate than the desired olefins undergoing polymerization and therefore will contribute to a decrease in the selectivity of the membrane which is formed from the desired polymerized olefin. Other impurities such as aromatics, water, oxygen- and sulfur-containing compounds will have a tendency to react with the catalyst which is employed for the polymerization process and therefore will deactivate it.

One method of reducing the amount of impurities which may be present in the solvent system is to treat the solvent with sulfuric acid followed by neutralization with a basic compound, washing and drying followed by distillation from a trialkyl aluminum compound. Another method of effecting a purification of the solvent is to subject the solvent to a hydrogenation process by treatment with hydrogen in the presence of a nickel catalyst. In contradistinction to these prior methods of purifying a solvent system, it has now been discovered that any impurities which are present in a solvent system such as cyclohexane may be effectively removed by a treatment hereinafter set forth in greater detail whereby the solvent system may be successfully employed in a polymerization of specific olefins such as 4-methyl-1-pentene, to obtain a polymer which may be effectively used as a membrane in the separation of gases, said membrane possessing an excellent selectivity value.

The purification of the solvent system is effected by treating a solvent such as, for example, cyclohexane which has a purity in the range of from about 98% to about 99.7% with anhydrous titanium tetrachloride, the anhydrous titanium tetrachloride being present in an amount in the range of from about 0.05% to about 0.6%, and preferably in a range of about 0.1% to about 0.3% by weight of the solvent. In the preferred embodiment of the invention, the treatment step is effected at ambient temperatures and atmospheric pressure, although it is contemplated that elevated temperatures and pressures may be used without deviating from the scope of the invention.

The addition of the titanium tetrachloride to the solvent will assist in the elimination of impurities such as isoparaffins, olefins, aromatics, oxygen, or sulfur-containing compounds, by forming a yellow complex and/or a precipitate. In the event that some water is present in the solvent system as an impurity, a small amount of hydrochloric acid is also formed. The removal of these impurities in the form of the complexes and/or precipitates is effected by contacting the treated solvent with an adsorbent, such as for example, by passing the solvent through a column of active silica gel under a slight pressure, that is, from about 0.5 to about 7 psi provided for by the introduction of a nitrogen atmosphere. Although the active silica gel constitutes the preferred adsorbent, it is also contemplated within the scope of this invention that any other types of adsorbents known in the art may also be employed to remove the complexes and the hydrochloric acid. Following passage through the active silica gel or other adsorbent, the effluent is then subjected to distillation, preferably in an inert atmosphere as provided for by a nitrogen blanket in the presence of a purification agent comprising an alkali metal borohydride or aluminum hydride which acts primarily as a reducing agent. Examples of these purification agents which may be employed will include compounds such as lithium borohydride, sodium borohydride, potassium borohydride, rubidium borohydride, cesium borohydride, lithium aluminum hydride, sodium aluminum hydride, potassium aluminum hydride, rubidium aluminum hydride, cesium aluminum hydride. The aforementioned hydrides will be present in the solvent system in an amount in the range of from about 0.05% up to about 0.5% and preferably in a range from about 0.1% to about 0.3% by weight. By utilizing a distribution system involving the purification agent of the type hereinbefore set forth, it is possible to remove any traces of hydrochloric acid or water which may still be present in the effluent from the percolation step as well as to reduce any residual olefinic hydrocarbon impurities which may still have been present after treatment with the titanium tetrachloride.

While the aforementioned procedure for purifying the solvent system is particularly effective for solvents which possess a purity of 98% or more, it is possible to purify solvents of less purity by a pretreatment procedure prior to the aforementioned steps of contacting with titanium tetrachloride and contact with an adsorbent followed by distillation in the presence of the purification agent. The pretreatment procedure which may be employed for solvents having less than 98% purity involves a washing of the solvent with a 1:1 sulfuric acid solution, neutralizing the washed solvent with sodium carbonate, water washing the solvent until a neutral pH has been attained followed by drying with anhydrous sodium sulfate and molecular sieves. Following the pretreatment of the solvent, it may then be further purified according to the process of this invention. Likewise, it is also contemplated within the scope of this invention that solvents which possess a purity greater than about 99.7% may be purified by only distillation in the presence of a purification agent of the type hereinbefore set forth, omitting the treatment with titanium tetrachloride and subsequent contact with an adsorbent.

The solvent thus purified may be utilized in a polymerization reaction in which an olefinic hydrocarbon such as, for example, 4-methyl-1-pentene is treated at polymerization conditions in the presence of a polymerization catalyst. As an example, the olefinic hydrocarbon undergoing polymerization is placed in an appropriate apparatus such as a reaction flask which is provided with heating and stirring means along with a polymerization catalyst lithium aluminum tetra(decyl) and the solvent such as cyclohexane. The polymerization reaction is allowed to proceed in an inert atmosphere such as that afforded by the introduction of nitrogen into the reaction flask for a predetermined period of time which may range from about 0.5 up to about 6 hours. The polymerization conditions which are employed to effect the desired reaction will include temperatures in the range of from about ambient to about 50° C. and pressures which may range from about atmospheric to about 1000 pounds per square inch (psi). After the desired reaction time has elapsed, the reaction is quenched by the addition of a mixture of alcohols such as methyl alcohol and isopropyl alcohol, filtered from the quench solution and solvent and after washing, the desired polymer is dried and recovered. As hereinbefore set forth, by utilizing a solvent which has been purified according to the process of the present invention, it is possible to effect the polymerization reaction in such a manner so that the polymer which is obtained will possess a desirable molecular weight and a predominately crystalline structure which will enable its use as a finely permeable barrier in the production of a membrane suitable for use in gas separation processes.

The following examples are given for purposes of illustrating the process of the present invention in which an organic solvent suitable for use as a medium in a polymerization reaction is purified to remove undesirable contaminants therefrom. However, it is to be understood that these examples are merely illustrative in nature and that the present process is not necessarily limited thereto.

EXAMPLE I

In this example, 5 mL of anhydrous titanium chloride was added to 3600 mL of a 99% pure cyclohexane. After thorough admixture, the solution which was pale yellow in color was passed through a column of active silica gel of a mesh size of 100–200. After the effluent had reached the bottom of the column, a nitrogen pressure of 7 psi was applied in order to facilitate the percolation through the column. The effluent in an amount of 2200 mL was mixed with 5 grams of lithium aluminum hydride and subjected to distillation at a temperature of about 40° C. under a reduced pressure of about 200 torr, the distillation being effected under a nitrogen blanket. A portion of the distillate in an amount of 2 mL was tested by adding a drop of acetic acid and two drops of titanium tetrachloride. The solution remained clear, thus showing a negative test for the presence of impurities such as olefins, aromatics, hetero compounds and water.

EXAMPLE II

To illustrate the utility of a solvent purified in accordance with the method set forth in Example I above to act as a solvent for a polymerization reaction, 60 mL of cyclohexane which had been treated according to Example I was injected into a nitrogen purged flask. Thereafter, 5 mL of a 1.0 M titanium tetrachloride solution in purified cyclohexane was also injected into the flask, no discoloration being observed and thus verifying the absence of any contaminants. Following this, 25 mL of a 0.2 M lithium aluminum tetra(decyl) solution was injected and a brown precipitate formed in the flask. The feed stream comprising 20 mL of 4-methyl-1-pentene and 0.2 mL of isoprene were injected into the flask and the reaction was allowed to proceed for a period of one hour. During this reaction period, dispersed solids were formed in the reaction mixture. At the end of the one hour period, the reaction was quenched by the addition of 50 mL of a solution containing methyl alcohol and isopropyl alcohol. The solids were recovered and washed in a blender five times with methyl alcohol followed by drying in a high vacuum to yield 6.7 grams of a white powder. The white powder which comprised poly(methylpentene) was dissolved in cyclohexane and poly(methylpentene) films were cast from a 1% solution of the polymer in the cyclohexane. The films were used to form a membrane by casting the poly(methylpentane) film on one surface of a finely porous support member comprising polysulfone. The resulting membrane in which the poly(methylpentene) film had a thickness of 11,920 Angstroms was used in a single stage gas separation process. A feed stream comprising air was passed over the surface of the membrane at a pressure of 20 psi and a temperature of 25° C. The selectivity factor which is a ratio of the oxygen to the nitrogen flow was 4.2.

EXAMPLE III

In this example, a nontreated cyclohexane solvent which showed a positive titanium tetrachloride test was used as a solvent in the polymerization of 4-methyl-1-pentene. The 4-methyl-1-pentene was polymerized in a manner similar to that set forth in Example II above, and the poly(methylpentene) which was formed was cast on a finely porous support member comprising polysulfone to form a gas membrane. The gas membrane thus formed was used in a single stage gas separation process under similar conditions to those hereinbefore set forth. The membrane, while exhibiting a higher permeability to oxygen than to nitrogen, only had an oxygen selectivity factor of 1.8.

EXAMPLE IV

In a manner similar to that set forth in Example 1 above, 3600 mL of 99% pure cyclohexane was treated with 5 mL of anhydrous titanium chloride. The resulting solution which was pale yellow in color was also passed through a 2'×30 mm column of activated silica gel which had a mesh size of 100–200. After the effluent had reached the bottom of the column, nitrogen pressure of 7 psi was applied to aid in the percolation. The effluent which was recovered from this step was admixed with 5 grams of sodium borohydride and subjected to distillation under a reduced pressure of about 200 torr at a temperature of about 40° C. A portion of the distillate which was recovered was tested by adding a drop of acetic acid and 2 drops of titanium tetrachloride. The solution remained clear and water-white, thus showing that no impurities were present in the distillate.

We claim as our invention:

1. A method for the purification of cyclohexane which comprises treating said cyclohexane with titanium tetrachloride, contacting said treated cyclohexane with an adsorbent, subjecting said cyclohexane to fractional distillation in the presence of a purification agent comprising an alkali metal borohydride or aluminum hydride to remove contaminants therefrom, and recovering the purified cyclohexane.

2. The method as set forth in claim 1 in which said distillation is effected at pressures in the range of from subatmospheric to about atmospheric pressure.

3. The method as set forth in claim 1 in which said adsorbent comprises activated silica gel.

4. The method as set forth in claim 1 in which said purification agent comprises sodium borohydride.

5. The method as set forth in claim 1 in which said purification agent comprises potassium borohydride.

6. The method as set forth in claim 1 in which said purification agent comprises lithium aluminum hydride.

7. The method as set forth in claim 1 in which said purification agent comprises sodium aluminum hydride.

8. The method as set forth in claim 1 in which said purification agent is lithium borohydride.

* * * * *